(12) United States Patent
Ochiai et al.

(10) Patent No.: US 7,718,635 B2
(45) Date of Patent: May 18, 2010

(54) TRITERPENIC ACID DERIVATIVE AND PREPARATION FOR EXTERNAL APPLICATION FOR SKIN COMPRISING THE SAME

(75) Inventors: Michio Ochiai, Yokohama (JP); Kenichi Goto, Yokohama (JP); Yoshihiro Tokudome, Yokohama (JP); Shigenari Hirokawa, Yokohama (JP)

(73) Assignee: Pola Chemical Industries Inc., Shizuoka-shi, Shizuoka (JP)

( * ) Notice: Subject to any disclaimer, the term of this patent is extended or adjusted under 35 U.S.C. 154(b) by 97 days.

(21) Appl. No.: 11/912,477

(22) PCT Filed: Apr. 13, 2006

(86) PCT No.: PCT/JP2006/307818

§ 371 (c)(1), (2), (4) Date: Oct. 24, 2007

(87) PCT Pub. No.: WO2006/132033

PCT Pub. Date: Dec. 14, 2006

(65) Prior Publication Data

US 2009/0075946 A1   Mar. 19, 2009

(30) Foreign Application Priority Data

Jun. 10, 2005   (JP) .............................. 2005-170220

(51) Int. Cl.
*A61K 31/66* (2006.01)
*C07C 61/12* (2006.01)

(52) U.S. Cl. ...................................... 514/120; 562/498

(58) Field of Classification Search ................. 562/498; 514/120

See application file for complete search history.

(56) References Cited

U.S. PATENT DOCUMENTS 4,857,554 A * 8/1989 Kallimanis .................. 514/557

FOREIGN PATENT DOCUMENTS

| JP | 08-165231 | 6/1996 |
| JP | 08-208424 | 8/1996 |
| JP | 11-012122 | 1/1999 |
| JP | 2000-302659 | 10/2000 |
| JP | 2004-131403 | 4/2004 |
| JP | 2004-331593 | 11/2004 |
| WO | WO 93/03731 | 3/1993 |
| WO | WO 01/72265 | 4/2001 |
| WO | WO 2004/047792 | 6/2004 |

OTHER PUBLICATIONS

Eugster et al., 1998, CAS: 129: 166219.*
Oyo Seikagaku Kenkyusho's, 1986, CAS: 104:39718.*
International Search Report dated Jul. 6, 2006.

* cited by examiner

*Primary Examiner*—Rei-tsang Shiao
(74) *Attorney, Agent, or Firm*—Knobbe, Martens, Olson & Bear, LLP

(57) ABSTRACT

In a triterpenic acid having hydroxyl groups, at least one of the hydroxyl groups is phosphorylated to produce a phosphorylated triterpenic acid and/or a salt thereof, thereby improving the solubility of the triterpenic acid in a preparation for external application for the skin and allowing the physiological activity of the triterpenic acid to be exerted satisfactorily. The phosphorylated triterpenic acid is preferably, for example, ursolic acid phosphate and/or a salt thereof. The preparation for external application for the skin is preferably a cosmetic, particularly preferably a quasi-drug.

6 Claims, No Drawings

TRITERPENIC ACID DERIVATIVE AND PREPARATION FOR EXTERNAL APPLICATION FOR SKIN COMPRISING THE SAME

Related Applications

This application is the U.S. National Phase under 35 U.S.C. §371 of International Application PCT/JP2006/307818, filed Apr. 13, 2006, which was published in a non-English language, which claims priority to JP Application No. 2005-170220, filed Jun. 10, 2005.

TECHNICAL FIELD

The present invention relates to a novel triterpenic acid derivative and a preparation for external application for skin containing the same.

BACKGROUND ART

A triterpenic acid such as ursolic acid has been known to have various physiological effects such as antioxidative effect, anti-inflammatory effect, and melanin production suppression effect, and technologies to blend the triterpenic acid into a preparation for external application for skin such as cosmetics have been known (see Patent Documents 1, 2, 3, 4, and 5, for example). However, the compounds have insufficient solubility in both an oily ingredient and an aqueous ingredient, and have a problem of precipitation of a triterpenic acid during long-term preservation. Physiological activities of a triterpenic acid may be reduced due to insufficient solubility, resulting in the insufficient physiological effects. Under such circumstances, the solubility of a triterpenic acid in an oily ingredient was improved by, for example, esterifying a triterpenic acid to yield a derivative of the triterpenic acid. However, this method is not considered to be satisfactory for preventing precipitation of a triterpenic acid (see Patent Document 6, for example). That is, there has been required means for improving solubility in a preparation without impairing physiological activities of a triterpenic acid such as ursolic acid that is known to have various physiological activities.

On the other hand, technologies to phosphorylate a compound having hydroxyl groups to obtain a phosphate have been known, and in the cosmetic fields, chemical modifications into phosphate derivatives are performed to stabilize sugars or sugar analogues such as ascorbic acid (see Patent Documents 7 and 8, for example). However, there are no examples of phosphorylation for improving solubility, and a phosphorylated compound of a triterpenic acid is a novel compound that has not been described in documents.

Patent Document 1: JP 08-165231 A
Patent Document 2: JP 08-208424 A
Patent Document 3: JP 01/072265 A1
Patent Document 4: JP 11-012122 A
Patent Document 5: JP 2000-302659 A
Patent Document 6: JP 2004-331593 A
Patent Document 7: JP 11-158197 A
Patent Document 8: JP 2001-354513 A

DISCLOSURE OF THE INVENTION

The present invention has been made under the circumstances described above, and an object of the present invention is to provide a technology of improving solubility of a triterpenic acid such as ursolic acid that is known to have various physiological activities without impairing the physiological activities.

In view of such circumstances, the inventors of the present invention have made extensive studies in order to find out a technology to improve solubility of a triterpenic acid having hydroxyl groups such as ursolic acid that is known to have various physiological activities without impairing the physiological activities, and as a result, the inventors found that a phosphorylated triterpenic acid obtained by phosphorylating at least one of hydroxyl groups in a triterpenic acid has such properties, thereby completing the present invention. That is, the present invention is as follows.

(1) A phosphorylated triterpenic acid, which is derived from a triterpenic acid having hydroxyl groups and obtained by phosphorylation at least one of the hydroxyl groups, and/or a salt thereof.

(2) The phosphorylated triterpenic acid and/or a salt thereof according to Item (1), which is ursolic acid phosphate and/or a salt thereof.

[Chemical formula 1]

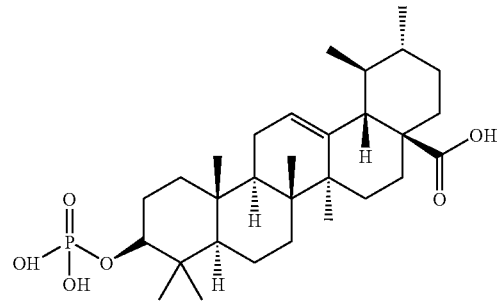

Ursolic acid phosphate (3) A preparation for external application for skin comprising the phosphorylated triterpenic acid and/or a salt thereof according to Item (1) or (2).

(4) The preparation for external application for skin according to Item (3), which is a cosmetic.

(5) The preparation for external application for skin according to Item (4), wherein the cosmetic is a quasi-drug.

(6) The preparation for external application for skin according to Item (5), which is for anti-inflammation.

(7) The preparation for external application for skin according to Item (5), which is for suppression of melanin production.

BEST MODE FOR CARRYING OUT THE INVENTION (1) Compound of the Present Invention A compound of the present invention is a phosphorylated triterpenic acid obtained by phosphorylating, in a triterpenic acid having hydroxyl groups (hereinafter, sometimes simply referred to as triterpenic acid), at least one of the hydroxyl groups. The triterpenic acid having hydroxyl groups is not particularly limited as long as it is used in the field of preparations for external application for skin such as cosmetics, and preferable examples thereof include ursolic acid, oleanolic acid, betulinic acid, and asiatic acid ((2α,3β,4α)-2,3,23-trihydroxy-12-en-ursolic acid ((2α,3β,4α)-2,3,23-trihydroxyurs-12-en-28-oic acid)). Of those, ursolic acid is particularly preferable because it is sold as a reagent and readily available, and has particularly significant physiological activities as a preparation for external application for skin.

Derivation of a triterpenic acid phosphate from a triterpenic acid may be performed in accordance with a generally known phosphorylation method. For example, a triterpenic acid is treated with a one to three-fold equivalent of diethyl-N,N-diethylphosphoramidate in the presence of tetrazole, and allowed to react with t-butylhydroperoxide to yield methyl phosphate of a triterpenic acid, and then bromotrimethylsilane was allowed to react therewith, to thereby yield a triterpenic acid phosphate.

Ursolic acid phosphate obtained by treating ursolic acid in this way has the structure shown above. The thus-obtained phosphorylated triterpenic acid may be converted into a salt by allowing the acid to react with an alkaline that is generally used in drugs or cosmetics. Preferable examples of such a salt include: alkaline metal salts such as sodium salts and potassium salts; alkali earth metal salts such as calcium salts and magnesium salts; organic amine salts such as ammonium salts, triethanolamine salts, and triethylamine salts; and basic amino acid salts such as lysine salts and arginine salts. The thus-obtained phosphorylated triterpenic acid or a salt thereof has significant solubility in an aqueous carrier and has significantly improved drug activity compared to a triterpenic acid. In a case of a preparation for external application for skin containing the phosphorylated triterpenic acid of the present invention, the phosphorylated triterpenic acid content is preferably from 0.001 to 0.1% by mass with respect to the total amount of the preparation for external application for skin. This is because if the content is too small, the drug activity may be not expressed, whereas if the content is too large, the drug activity may reach a plateau.

(2) Preparation for External Application for Skin of the Present Invention

The preparation for external application for skin of the present invention is characterized by containing the above-mentioned phosphorylated triterpenic acid of the present invention and/or a salt thereof. Examples of the preparation for external application for skin of the present invention include cosmetics and external medicines for skin, and of those, cosmetics are preferable. Among the cosmetics, quasi-drugs are preferable. The quasi-drugs are products considered to have specific effect and efficacy approved by the Japanese Pharmaceutical Affairs Law and have moderate effects compared to drugs. In the present invention, the quasi-drugs mean cosmetics to be used not only for beauty but also for prevention or improvement of specific symptoms. The preparation for external application for skin of the present invention also includes a cosmetic that is similar to a quasi-drug of Japan and is used for the same purposes. Examples of such a cosmetic include medicated cosmetics of Korea and drug-containing cosmetics of China.

In the preparation for external application for skin of the present invention, a phosphorylated triterpenic acid and/or a salt thereof, serving as an essential ingredient, has anti-inflammatory effect and melanin production suppression effect, and therefore the preparation is preferably used as a preparation for external application for skin for anti-inflammation or a preparation for external application for skin for suppression of melanin production or for skin-whitening. Of those, preferable are a quasi-drug for anti-inflammation and a quasi-drug for suppression of melanin production, and the anti-inflammatory effect or melanin production suppression effect is preferably indicated in the packages or attached documents of such quasi-drugs. As a result, mode in use of the preparation for external application for skin can be clearly indicated, and a user can be urged to use it appropriately.

The preparation for external application for skin of the present invention may include not only the above-mentioned phosphorylated triterpenic acid and salt thereof but also various ingredients to be generally used in medicines or cosmetics, that is, one or more of the following: aqueous ingredients, oily ingredients, powder ingredients, surfactants, humectants, thickeners, coloring materials, flavors, antioxidants, pH adjusters, chelating agents, antiseptics, and drugs such as ultraviolet protective agents, anti-inflammatory agents, wound healing agents, metabolism enhancing agents, and skin-whitening agents.

Examples of the aqueous ingredients include water and lower alcohols (ethanol, propanol, and isopropanol).

Examples of the oily ingredients include higher fatty acids (such as stearic acid, palmitic acid, myristic acid, lauric acid, and esters thereof), higher alcohols (such as cetanol, lanolin alcohol, stearyl alcohol, and cetostearyl alcohol), waxes (such as hard paraffin, microcrystalline wax, ceresin wax, polyethylene wax, bees wax, vegetable wax, carnauba wax, and candelilla wax), natural or synthetic oily substances (such as squalane, liquid paraffin, lanolin or a derivative thereof, olive oil, camellia oil, cottonseed oil, oleyl alcohol, castor oil, petrolatum, diethoxyethyl adipate, silicon oil, and fluorohydrocarbon).

Examples of powder ingredients include aluminum oxide, titanium dioxide, zinc oxide, colcothar, yellow oxide, ultramarine, iron blue, acrylic resin powder, silica, talc, sericite, mica, and mica titanium.

Examples of surfactants include: anionic surfactants such as fatty acid soap (such as sodium laurate and sodium palmitate), potassium lauryl sulfate, and triethanolamine alkyl ether sulfate; cationic surfactants such as stearyltrimethylammonium chloride, benzalkonium chloride, and laurylamine oxide; amphoteric surfactants such as an imidazoline-based amphoteric surfactant (such as 2-cocoyl-2-imidazolinium hydroxide-1-carboxyethyloxy-2-sodium), a betaine-based amphoteric surfactant (such as alkyl betaine, amide betaine, and sulfobetaine), and acylmethyl taurine; nonionic surfactants such as sorbitan fatty esters (such as sorbitan monostearate and sorbitan sesquioleate), glycerin fatty acids (such as glycerin monostearate), propylene glycol fatty esters (such as propylene glycol monostearate), hydrogenated castor oil derivatives, glycerin alkyl ethers, polyoxyethylene (POE) sorbitan fatty esters (such as POE sorbitan monooleate and polyoxyethylene sorbitan monostearate), POE sorbite fatty esters (such as POE-sorbite monolaurate), POE glycerin fatty esters (such as POE-glycerin monoisostearate), POE fatty esters (such as polyethylene glycol monooleate and POE distearate), POE alkyl ethers (such as POE2-octyldodecyl ether), POE alkylphenyl ethers (such as POE nonylphenyl ether), Pluronics™, POE•POP alkyl ethers (such as POE•POP2-decyltetradecyl ether), Tetronics™, a POE castor oil-hydrogenated castor oil derivative (such as POE castor oil and POE hydrogenated castor oil), sucrose fatty esters, and alkylglycoside.

Examples of humectants include: polyalcohols such as glycerin, propylene glycol, 1,3-butylene glycol, dipropylene glycol, ethylene glycol, 1,4-butylene glycol, diglycerine, triglycerine, and polyethylene glycol; glucose, maltose, maltitol, sucrose, fructose, threitol, erythritol, sorbitol or derivatives thereof, starch-dissolving sugar, hyaluronic acid, chondroitin sulfate, hydrolyzed collagen, hydrolyzed ealstin, carboxylmethyl chitin, casein soda, mucin, glycosphingolipid. Those may be comprised in the range from 0.1 to 30% by weight with respect to all ingredients.

Examples of the thickeners include carboxyvinyl polymer, CP jelly, carboxymethyl cellulose, carrageenan, sodium alginate, bentonite, veegum, and synthetic hectorite.

Examples of antioxidants include dibutylated hydroxytoluene (BHT), buthylated hydroxyanisole (BHA), tocopherol sodium pyrosulfite, sodium sulfate, and tocopherol acetic acid.

Examples of pH adjusters include citric acid, lactic acid, tartaric acid, and phosphate.

Examples of chelating agents include ethylene diamine tetraacetic acid (EDTA).

Examples of antiseptics include methyl, ethyl, propyl, or butyl ester of p-oxybenzoic acid, phenoxyethanol, o-phenylphenol, dehydroacetic acid, or salts thereof, p-cresol, m-cresol, and o-chlor-m-xylenol.

Examples of the ultraviolet protective agents include urocanic acid or a derivative thereof, isoferulic acid or a salt thereof, oxybenzone or a derivative thereof, p-aminobenzoic acid or a derivative thereof, dibenzoylmethane or a derivative thereof, and p-methoxycinnamic acid or a derivative thereof. Those may be comprised in the range from 0.01 to 30% by weight with respect to all ingredients.

Examples of the anti-inflammatory agents include glycyrrhetinic acid or a derivative thereof such as stearyl glycyrrhetinate, glycyrrhizinic acid or a salt thereof, horse chestnut extract, and aloe extract. Those may be comprised in the range of from 0.01 to 5% by weight with respect to all ingredients.

Examples of the wound healing agents include royal jelly extract, Angelica root extract, rosemary extract, and rosmarinic acid. Those may be comprised in the range of from 0.01 to 5% by weight with respect to all ingredients.

Examples of the metabolism enhancing agents include placenta extract, γ-oryzanol, an amino acid or a derivative thereof, and vitamin E or a derivative thereof. Those may be comprised in the range of from 0.01 to 5% by weight with respect to all ingredients.

Examples of skin-whitening agents include pantetheine-S-sulfonic acid, ascorbic acid, or magnesium phosphate thereof, arbutin, kojic acid, linoleic acid, tranexamic acid, and esculin.

Among the above-mentioned arbitrary ingredients, in particular, an active ingredient for anti-inflammatory is preferably used in a quasi-drug for anti-inflammatory. Preferable examples of such an active ingredient include stearyl glycyrrhetinate and dipotassium glycyrrhizinate. The concentration of such an active ingredient is preferably 0.01 to 5% by mass.

In addition, an active ingredient for suppression of melanin production or for skin-whitening is particularly preferably used in a quasi-drug for suppression of melanin production. Examples of such an active ingredient include ascorbic acid and a salt thereof, ascorbic acid phosphate and a salt thereof, ascorbic acid glucoside and a salt thereof, arbutin and a salt thereof, ellagic acid and a salt thereof, tranexamic acid and a salt thereof, and 4-methoxysalicylic acid and a salt thereof. The concentration of such an active ingredient is preferably 0.01 to 5% by mass.

The preparation for external application for skin of the present invention can be produced by treating the above-mentioned essential ingredients and arbitrary ingredients in accordance with a conventional method.

Hereinafter, the present invention will be described in more detail by way of examples, but the present invention should not be limited only to such examples.

EXAMPLES

Example 1

A mixture of ursolic acid (48.1 g, 0.105 mol), dimethyl-N, N-diethylphosphoramidate (34.82 g, 0.211 mol), dry tetrahydrofuran (1,250 ml) was heated to 35° C. to prepare a clear solution, and 1H-tetrazole (44.25 g, 0.632 mol) was added at a time at an internal temperature of 27° C., followed by stirring at room temperature (22° C.) for one hour. After confirming generation of dimethyl phosphite by TLC, the reaction solution was cooled with acetone-dry ice, and an aqueous solution of 70% t-butyl hydroperoxide (84 mL, 0.607 mol) was added dropwise thereto at −20° C. The ice bath was removed to gradually increase the temperature to room temperature, and TLC was performed to confirm disappearance of dimethyl phosphite and generation of dimethyl phosphate, followed by stopping the reaction at 0° C. with an aqueous solution of 10% sodium hydrogensulfite (300 ml). Ethyl acetate (1,250 mL) was added to the reaction solution, and the organic layer was separated. The organic layer was washed sequentially with an aqueous solution of 10% sodium hydrogensulfite (100 ml×3), an aqueous solution of 5% sodium hydrogen carbonate (200 ml×3), and a saturated salt solution, and dried with anhydrous magnesium sulfate. Subsequently, silica gel (400 mL) was added to the organic layer, followed by concentration and drying under reduced pressure. A column was filled with silica gel absorbing the organic layer and then filled with hexane. Then, the column was further filled with hexane to elute non-adsorbed substances, and the development with hexane/ethyl acetate (2:1) was performed. Among eluted fractions, fractions having a single ingredient were concentrated, to thereby yield 35 g of a titled compound as gel powder. This product was found by using NMR to absorb ethyl acetate and dichloromethane used in washing. Further, fractions containing traces of impurities were obtained, to thereby yield 6 g of the compound. The thus-synthesized ursolic acid 3-methylphosphate (35 g, 62 mmol) was dissolved in dry dichloromethane (350 ml), and bromotrimethylsilane (25 mL, 186 mmol) was added in a stream of argon, followed by a reaction at room temperature for one hour. After TLC confirmation, the reaction solution was concentrated under reduced pressure, and the residue was dissolved in dry toluene and concentrated (200 ml×2) to completely remove excessive bromotrimethylsilane. The concentrate was dissolved in 95% methanol (300 mL), and the solution was stirred at room temperature for one hour, to thereby precipitate crystals. The solution was concentrated under reduced pressure and dried with phosphoric acid anhydride at 50° C. overnight under reduced pressure, to thereby yield 23.5 g of ursolic acid phosphate.

$^1$H-NMR (ppm): 5.23 (m, 1H), 3.87 (m, 1H), 2.20 (d, 1H), 2.05-1.25 (m, 25H), 1.12 (s, 3H), 1.02 (s, 3H), 0.99 (s, 3H), 0.97 (d, 3H), 0.87 (d, 3H), 0.85 (s, 3H), Mass: 535 (M$^+$) IR (cm$^{-1}$): 2948, 1694, 1456, 1378, 1028, 661, 566

Test Example 1

The thus-obtained ursolic acid phosphate was compared to ursolic acid (control) on their solubilities. 20 mg of ursolic acid phosphate or ursolic acid was placed in a 2-mL glass container, and the solvents shown in Table 1 were added thereto. The mixture was stirred for 16 hours and was passed through a 0.45-μm filter. After that, concentration measurement was performed by HPLC. The results are shown in Table 1. The results revealed that solubility of ursolic acid phosphate of the present invention has been improved compared to that of ursolic acid.

TABLE 1

Comparison of solubilities
Saturated concentration (μg/mL)

| Solvent | pUA | UA |
| --- | --- | --- |
| EtOH | >100000 | <1 |
| 8% EtOH/DW | 134.9 | <1 |
| DW | 20.1 | <1 |
| 8% EtOH/0.1 M phosphate Buffer (pH9) | 7.5 | <1 |
| 0.1 M phosphate Buffer (pH9) | 119.7 | <1 |
| 8% EtOH/0.1 M phosphate Buffer (pH7.0) | 31.1 | <1 | pUA (ursolic acid phosphate)
UA (ursolic acid)

Test Example 2

A guinea pig maximization test was performed using ten Hartley white guinea pigs to examine the presence or absence of the skin sensitivity of ursolic acid phosphate to the guinea pigs. An emulsified product containing distilled water and Freund's complete adjuvant (FCA) in equal volumes, a test substance (dissolved in olive oil, 5%), and a mixture including a test substance and FCA in equal volumes were separately injected intracutaneously to five guinea pigs in two sites with 0.1 mL, respectively. The next day, the hair of the intracutaneous injection sites was shaved, and a mixture of 10% sodium lauryl sulfate/petrolatum was applied thereto. The day after that, 0.1 ml of 5% ursolic acid phosphate (dissolved in olive oil) was applied with a patch for 48 hours to the shaved sites to complete induction of sensitization. After completion of induction of sensitization, a 10-day rest period was provided. After completion of the period, the hair in back untreated sites was shaved. Then, each of 0.1 ml of 5%, 0.5%, and 0% ursolic acid phosphate (dissolved in olive oil) was applied with a patch for 24 hours to respective three sites to induce sensitization. Thirty minutes and 24 hours after patch removal, skin reactions were observed. Observation of skin reactions was performed according to Draize criteria (−: no reaction, ± reaction with suspected erythema, +: reaction with clear erythema, ++: reaction with edema, papule, or desquamation). As a result, there were no differences between sample-administered group and control group with regard to the skin reactions, and in this experiment, the sensitization of ursolic acid phosphate to skin was not observed.

Example 2

An anti-inflammatory lotion, which is a preparation for external application for skin of the present invention, was prepared according to the following formulation. That is, the formulation ingredients were heated to 80° C. and mixed well, followed by cooling with stirring, to thereby yield Lotion 1. In Comparative Example 1, where ursolic acid phosphate was replaced by ursolic acid, the same procedures as above were performed to thereby prepare a lotion of Comparative Example 1. Lotion 1 was clear even after three-month preservation at 5° C., 20° C., and 40° C., and was found to be stable, while the lotion of Comparative Example 1 became turbid immediately after production.

| | |
| --- | --- |
| 1,3-butanediol | 8% by mass |
| 1,2-pentanediol | 2% by mass |
| Phenoxyethanol | 0.5% by mass |
| 1% Dipotassium glycyrrhizinate solution | 5% by mass |
| Glycerin | 3% by mass |
| 1% Ursolic acid phosphate solution | 1% by mass |
| POE(60) hydrogenated castor oil | 0.1% by mass |
| Water | 80.4% by mass |

Test Example 3

Twenty panelists with skin disorders were divided into two groups consisting of 10 panelists each. The panelists of one group used Lotion 1 continuously for two weeks, while the panelists of the other group used the lotion of Comparative Example 1 continuously for two weeks, followed by observation of variations in conditions of skin disorders.

Three specialists judged the conditions of skin disorders from images of cheeks enlarged by a video microscope based on scores according to the following criteria. During this test, a panelist who felt uncomfortable in the skin stopped the test at the time, and was judged as a dropout case. The results are shown in Table 2. The results revealed that a quasi-drug of the present invention has an anti-inflammatory effect equal to or more than that of one containing ursolic acid. In the case of Lotion 1, there was not dropout case, while in the case of Comparative Example 1, there was one dropout case.

(Criteria)
Score 1: Significant skin disorder
Score 2: Obvious skin disorder
Score 3: Minor skin disorder
Score 4: Healthy skin

TABLE 2

| | | Evaluation results | | | |
| --- | --- | --- | --- | --- | --- |
| | | Score 1 | Score 2 | Score 3 | Score 4 |
| Lotion 1 | Before test | 2 | 8 | | |
| | After test | | 6 | 2 | 2 |
| Comparative example 1 | Before test | 2 | 8 | | |
| | After test | | 7 | 1 | 1 |

Example 3

An anti-inflammatory lotion, which is a preparation for external application for skin of the present invention, was prepared according to the following formulation. That is, formulation ingredients were heated to 80° C. and mixed well, and the components (ii) were added to the components (i), followed by neutralization. Then, the components (iii) were added thereto with vigorous stirring to emulsify the mixture, and the mixture was cooled with stirring, to thereby yield Emulsion 1. In Comparative Example 2, where ursolic acid phosphate was replaced by ursolic acid, the same procedures as above were performed to thereby prepare an emulsion of Comparative Example 2. The emulsions were stored at 5° C., 20° C., and 40° C. for one month. As a result, there was no change in Emulsion 1, while insoluble "grains" were precipitated in the emulsion of Comparative Example 2 under all the temperature conditions.

(i)

| | |
|---|---|
| Alkyl acrylate (10 to 30 carbon atoms)•acrylic acid copolymer (PEMLEN TR-2 manufactured by Goodrich Corporation) | 0.4% by mass |
| Polyethylene glycol 1500 | 0.5% by mass |
| 1,3-butanediol | 5% by mass |
| Glycerine | 8% by mass |
| Maltitol | 0.4% by mass |
| 1% Hydroxyproline solution | 0.2% by mass |
| 1% Serine solution | 0.2% by mass |
| 1% Glycine solution | 0.2% by mass |
| Saccharide isomerate (PENTAVITIN manufactured by Pentapharm Corporation) | 0.1% by mass |
| Polyoxyethylene(60) hydrogenated castor oil | 0.3% by mass |
| Methyl gluceth-20 | 0.5% by mass |
| POP(23)POE(34)stearyl | 0.2% by mass |
| Ursolic acid phosphate | 0.3% by mass |
| Water | 77.1% by mass |

(ii)

| | |
|---|---|
| 10% Potassium hydroxide solution | 3% by mass |
| Water | 7% by mass |

(iii)

| | |
|---|---|
| Liquid paraffin | 5% by mass |
| Behenyl alcohol | 1% by mass |
| Selachyl alcohol | 0.5% by mass |
| Stearyl glycyrrhetinate | 0.1% by mass |

Example 4

A lotion for suppression of melanin production, which is a preparation for external application for skin of the present invention, was prepared according to the following formulation. That is, the formulation ingredients were heated to 80° C. and mixed well, followed by cooling with stirring, to thereby yield Lotion 2. In Comparative Example 3, where ursolic acid phosphate was replaced by ursolic acid, the same procedures as above were performed to thereby prepare a lotion of Comparative Example 3. Lotion 2 was clear even after three-month preservation at 5° C., 20° C., and 40° C., and was found to be stable, while the lotion of Comparative Example 3 became turbid immediately after production.

| | |
|---|---|
| 1,3-butanediol | 8% by mass |
| 1,2-pentanediol | 2% by mass |
| Phenoxyethanol | 0.5% by mass |
| Ascorbic acid glucoside | 5% by mass |
| Glycerine | 3% by mass |
| 1% Ursolic acid phosphate solution | 1% by mass |
| POE(60) hydrogenerated castor oil | 0.1% by mass |
| Water | 80.4% by mass |

Example 5

A lotion for suppression of melanin production, which is a preparation for external application for skin of the present invention, was prepared according to the following formulation. That is, the formulation ingredients were heated to 80° C. and mixed well, followed by cooling with stirring, to thereby yield Lotion 3. In Comparative Example 4, where ursolic acid phosphate was replaced by ursolic acid, the same procedures as above were performed to thereby prepare a lotion of Comparative Example 4. Lotion 3 was clear even after three-month preservation at 5° C., 20° C., and 40° C., and was found to be stable, while the lotion of Comparative Example 4 became turbid immediately after production.

| | |
|---|---|
| 1,3-butanediol | 8% by mass |
| 1,2-pentanediol | 2% by mass |
| Phenoxyethanol | 0.5% by mass |
| Ascorbic acid-2-Phosphate magnesium potassium | 5% by mass |
| Glycerine | 3% by mass |
| 1% Ursolic acid phosphate solution | 1% by mass |
| POE(60) hydrogenerated castor oil | 0.1% by mass |
| Water | 80.4% by mass |

Example 6

A lotion for suppression of melanin production, which is a preparation for external application for skin of the present invention, was prepared according to the following formulation. That is, the formulation ingredients were heated to 80° C. and mixed well, followed by cooling with stirring, to thereby yield Lotion 4. In Comparative Example 5, where ursolic acid phosphate was replaced by ursolic acid, the same procedures as above were performed to thereby prepare a lotion of Comparative Example 5. Lotion 4 was clear even after three-month preservation at 5° C., 20° C., and 40° C., and was found to be stable, while the lotion of Comparative Example 5 became turbid immediately after production.

| | |
|---|---|
| 1,3-butanediol | 8% by mass |
| 1,2-pentanediol | 2% by mass |
| Phenoxyethanol | 0.5% by mass |
| Arbutin | 2% by mass |
| Glycerine | 3% by mass |
| 1% Ursolic acid phosphate solution | 1% by mass |
| POE(60) hydrogenerated castor oil | 0.1% by mass |
| Water | 83.4% by mass |

INDUSTRIAL APPLICABILITY

The present invention can provide a technology to improve solubility of a triterpenic acid having hydroxyl groups such as ursolic acid that is known to have various physiological activities without impairing the physiological activities. A preparation for external application for skin of the present invention can be suitably applied to cosmetics (quasi-drugs) for anti-inflammation or for suppression of melanin production.

What is claimed is:

1. A composition for external application for skin, comprising ursolic acid phosphate and/or a salt thereof;

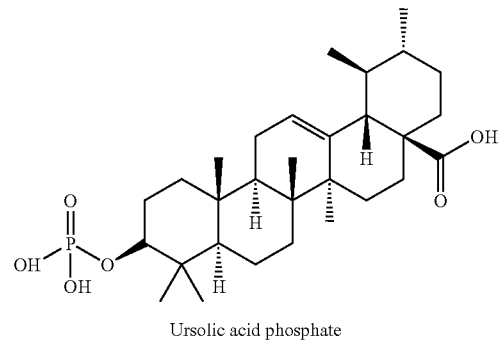

Ursolic acid phosphate and a suitable carrier.

2. The composition for external application for skin according to claim 1, which is a cosmetic.

3. The composition for external application for skin according to claim 1 or 2, which is for anti-inflammation.

4. The composition for external application for skin according to claim 1 or 2, which is for suppression of melanin production.

5. A method of treating a skin disorder comprising administering a composition comprising ursolic acid phosphate and/or a salt thereof to an individual in need thereof;

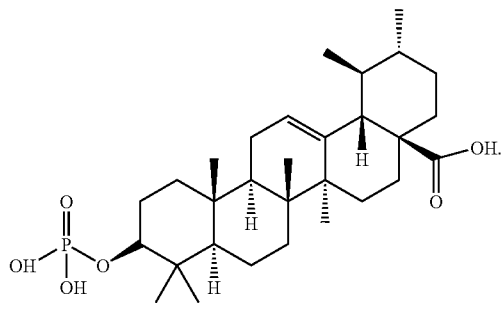

Ursolic acid phosphate

6. The method of claim 5, wherein the skin disorder is selected from inflammation and melanin production.

* * * * *

UNITED STATES PATENT AND TRADEMARK OFFICE
CERTIFICATE OF CORRECTION

PATENT NO.       : 7,718,635 B2                                    Page 1 of 1
APPLICATION NO.  : 11/912477
DATED            : May 18, 2010
INVENTOR(S)      : Ochiai et al.

It is certified that error appears in the above-identified patent and that said Letters Patent is hereby corrected as shown below:

Column 4, Line 47, "POE sorbite fatty" should be changed to --POE sorbitan fatty--

Column 4, Line 48, "such as POE sorbite" should be changed to --such as POE sorbitan--

Column 4, Line 55, "oil-hydrogenated castor" should be changed to --oil•hydrogenated castor--

Column 4, Line 64, "hydrolyzed ealstin," should be changed to --hydrolyzed elastin,--

Column 4, Line 65, "carboxylmethyl chitin," should be changed to --carboxymethyl chitin,--

Column 5, Line 5, "buthylated hydroxyanisole" should be changed to --butylated hydroxyanisole--

Column 5, Line 17, "and o-chlor-m-xylenol." should be changed to --and o-chloro-m-xylenol.--

Column 6, Line 59, "661, 566" should be changed to --661, 566.--

Column 7, Line 1, "a 0.45-µm filter." should be changed to --a 0.45 µm filter.--

Column 8, Line 9, "hydrogenerated castor oil" should be changed to --hydrogenated castor oil--

Column 9, Line 6, "coplymer (PEMLEN TR-2" should be changed to --copolymer (PEMULEN TR-2--

Column 9, Line 15, "hydrogenerated castor oil" should be changed to --hydrogenated castor oil--

Column 9, Line 50, "hydrogenerated castor oil" should be changed to --hydrogenated castor oil--

Column 10, Line 8, "hydrogenerated castor oil" should be changed to --hydrogenated castor oil--

Column 10, Line 34, "hydrogenerated castor oil" should be changed to --hydrogenated castor oil--

Signed and Sealed this

Sixteenth Day of November, 2010

David J. Kappos
*Director of the United States Patent and Trademark Office*